United States Patent [19]

Ishak

[11] Patent Number: 5,545,146
[45] Date of Patent: Aug. 13, 1996

[54] CATHETER APPARATUS HAVING A RETRACTABLE INTRAVENOUS NEEDLE ASSEMBLY

[76] Inventor: Noshi A. Ishak, 87 Spring St., Laconia, N.H. 03246

[21] Appl. No.: 264,017

[22] Filed: Jun. 22, 1994

[51] Int. Cl.⁶ ................................................ A61M 5/32
[52] U.S. Cl. .......................... 604/198; 604/164; 604/110
[58] Field of Search ................................. 604/110, 163, 604/104, 171, 192, 198, 263

[56] References Cited

U.S. PATENT DOCUMENTS

| | | | |
|---|---|---|---|
| 4,834,718 | 5/1989 | McDonald | 604/195 |
| 4,952,207 | 8/1990 | Lemieux | 604/164 |
| 5,108,376 | 4/1992 | Bonaldo | 604/171 |
| 5,137,515 | 8/1992 | Hogan | 604/110 |
| 5,176,655 | 1/1993 | McCormick et al. | 604/198 |
| 5,209,739 | 5/1993 | Talalay | 604/195 |
| 5,269,760 | 12/1993 | Bina | 604/110 |
| 5,314,503 | 5/1994 | Bobrove et al. | 604/164 |

*Primary Examiner*—Corrine M. McDermott
*Attorney, Agent, or Firm*—William B. Ritchie

[57] ABSTRACT

A catheter apparatus for intravenous applications, such as hemodialysis, which helps prevent needlesticks. The invention includes a hollow plunger to which a hollow needle is attached. A housing surrounds the plunger and contains a locking device so that when the plunger is retracted and the needle is pulled within the housing, the plunger becomes locked into place, thus encasing and securing the needle. A standard IV tubing line is attached to the apparatus, the introducing needle inserted so that the catheter is placed in position, and then the introducing needle is withdrawn and locked in place without the need for the operator having to break the system. Once the needle is locked into position, medical personnel are protected from a needlestick as the entire needle is within the apparatus.

1 Claim, 3 Drawing Sheets

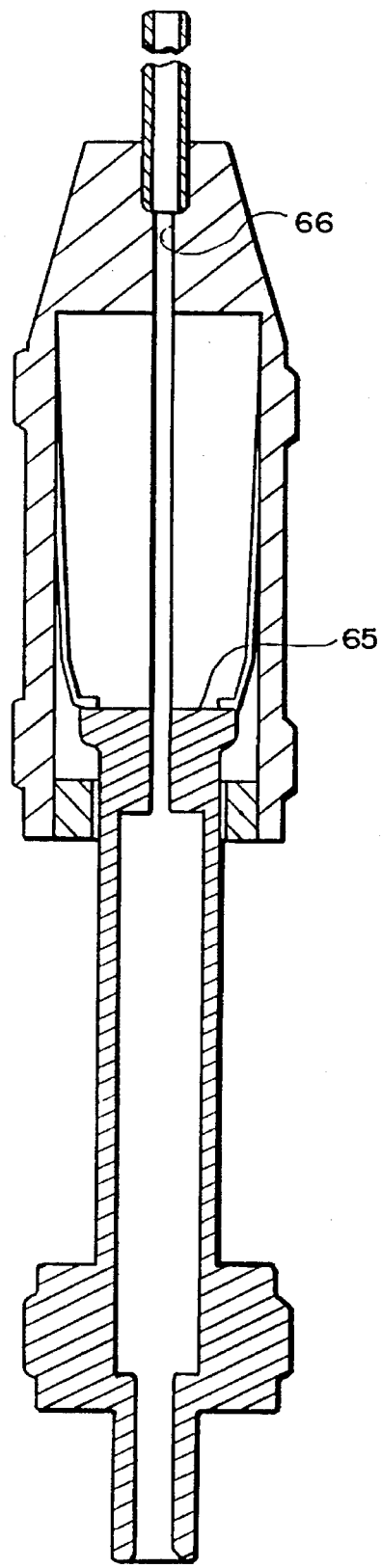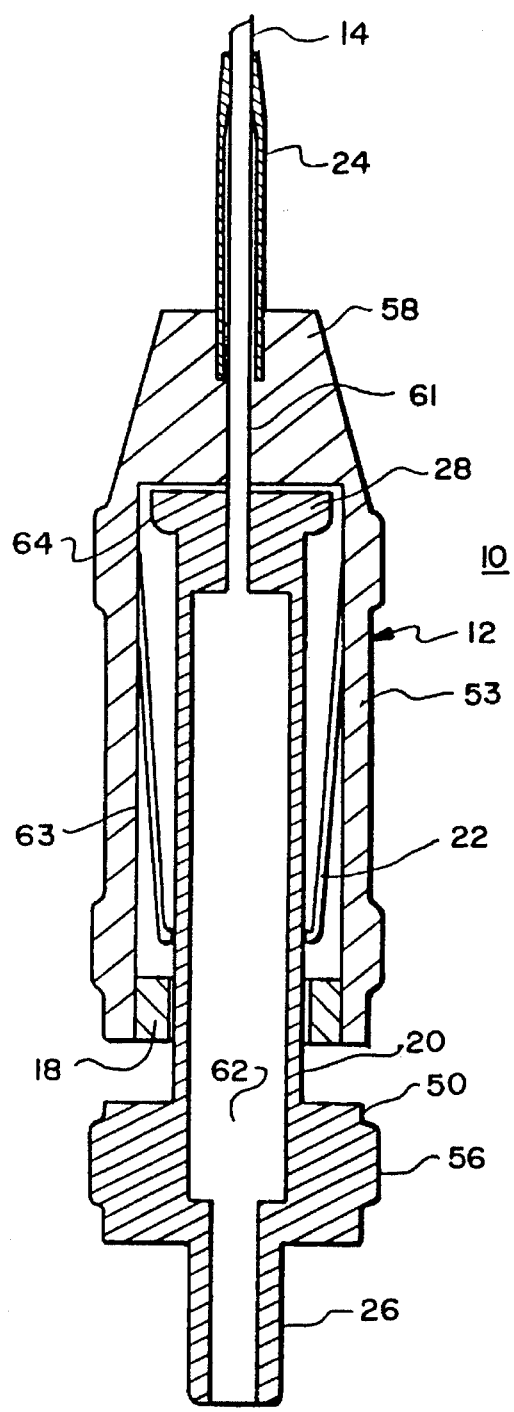
FIG. 3
FIG. 2

CATHETER APPARATUS HAVING A RETRACTABLE INTRAVENOUS NEEDLE ASSEMBLY

BACKGROUND OF THE INVENTION

1. Field of the Invention

The invention relates to catheters for intravenous applications.

2. Description of the Related Art

Each year, the number of individuals who are infected with Human Immuno-deficiency Virus (HIV), Hepatitis B (HPV), and other dangerous diseases is increasing. Currently, the Center for Disease Control (CDC) estimates that from 1.5–2 million people in the United States are infected with HIV. Many of these HIV cases are undiagnosed, which makes anyone who comes in contact with the infected person's body fluids vulnerable to HIV infection as well. Nurses and doctors are particularly vulnerable to HIV infection because their work involves working closely with the body fluids of their patients.

One significant source of HIV exposures for health care workers is accidental needlesticks. The number of accidental needlesticks is estimated to be more than one million per year.

Of these, roughly 2% are contaminated by HIV. To make matters worse, about 50% of HIV needlesticks go unreported. The significance of this problem is borne out by the fact that 80% of HIV exposures to health care workers are caused by needlesticks. Of these needlesticks, one in 200 results in an HIV infection. The CDC also estimates that 12,000 health care workers in the United States will become infected with HPV each year. Over 80% of those HPV infections acquired occupationally by health care workers will be as a result of needlesticks or other sharp instruments. Of those infected, over 200 will die. Clearly, there is a vital need for reducing the occurrence of this type of accident.

Studies reveal that more that 75% of needlesticks occur after use of the needle, in preparation for, or during disposal. Yet despite special precautions such as the use of containers for needles to be discarded and educational programs for health workers, the incidence of needlesticks has not been significantly reduced. Many experts predict that this situation will not change until needles and catheters of safer design are introduced.

Typical catheter designs for intravenous applications require that an introducing needle be used to create an opening in a vein into which the catheter can be inserted. The disadvantage of this approach is that body fluids can discharge from the opening while the needle is being withdrawn and the catheter inserted, thus risking exposure to the health care worker. Furthermore, neither the needle or catheter contains a means of protecting the worker from a needlestick.

Attempts have been made to provide a needle which can be withdrawn into a protective shield. A typical example of this type of apparatus is the PROTECTIV™ catheter marketed by Critikon, Inc. This device has an introducing needle which includes a protective guard for preventing contact with the needle during and after use. A catheter is attached to the needle, the needle is used to provide an introducing opening within the vein of a patient, and the catheter is inserted into this opening by sliding it off the needle as the needle is withdrawn into the protective guard. The needle is then removed from the catheter and discarded. However to complete the procedure, such devices, including the PROTECTIV™ design, requires that the user then attach the catheter to the intravenous tubing. During this attachment, the user is vulnerable to exposure to the patient's blood.

In the case of hemodialysis, this potential for the exposure discourages the use of catheters of this type. Instead, needles that are attached directly to intravenous tubing are preferably used. For hemodialysis patients, doctors must often perform surgery upon the patient to create a fistula. A fistula is a large, highly accessible vein, built from connecting one of the patient's veins with an artery, and designed to better accommodate numerous intravenous injections or withdrawals. Nevertheless, the introduction of the needle into the dialysis fistula risks causing significant local trauma of several varieties. Whenever a needle is inserted in the fistula, the potential for trauma to the fistula tissue exists. Further, when a needle is left in place during the hemodialysis procedure, it presents potential trauma since it may be moved to the point that it impacts or even penetrates the opposite wall of the fistula, thus leading to infiltration and bleeding. Furthermore, the removal of the dialysis needle is accompanied by applying pressure to the exit site, which usually traumatizes the inner surface of the fistula, resulting in a tendency for scarring of the fistula.

The repetitive traumatization of dialysis fistulas often leads to failure of the fistula, which is the primary cause of hospitalization for patients with End Stage Renal Disease. The use of catheters for hemodialysis offers significant advantage over metal needles. Since the catheter can be manufactured from a flexible, non-traumatizing material such as Teflon, the only trauma to the fistula is limited to the initial insertion of the introduction needle.

A device which allows placement of an intravenous tubing-connected catheter inside the vein without the need to remove the introducing needle, while allowing secure enclosure of the needle so as to prevent subsequent needlesticks is not disclosed in the prior art.

SUMMARY OF THE INVENTION

It is the object of the invention to provide a catheter apparatus which can place a catheter inside the patient' vein or fistula without requiring the removal of the introducing needle.

It is still another the object of the invention to provide a catheter apparatus which completely encloses the introducing needle after use so that it cannot produce a needlestick.

It is still another the object of the invention to provide a catheter apparatus which secures the introducing needle with the apparatus after use.

It is still another the object of the invention to provide a catheter apparatus which is substantially leak-free.

It is still another the object of the invention to provide a catheter apparatus which can be connected to intravenous tubing prior to insert the catheter in the patient.

It is still another the object of the invention to provide a catheter apparatus that enables the viewing of the flashback of blood once the introducing needle has been introduced into the vein.

The invention is an apparatus for intravenous medical procedures. A housing having a barrel with an interior cross-section is provided. The housing has a tip at one end and a plunger opening at the other end. Tip of said housing has a tip bore with a diameter. The tip bore extends into the barrel of said housing. A plunger having a needle opening, and an intravenous tubing line opening is provided. Said plunger has an exterior cross-section corresponding to the interior cross-section of the barrel of said housing. An introducing needle having a point and a gauge size corresponding to the diameter of the tip bore is provided. Said needle is rigidly connected to the needle opening of said plunger, such that when said plunger is fully inserted into the barrel of said housing, said needle extends through said tip bore. Locking means for holding said plunger in a fixed retracted position relative to said housing is provided. When said plunger is in the fixed retracted position, the point of said introducing needle is held within the tip bore of said housing. A flexible catheter, having a venous end and an attachment end is provided. The attachment end of said catheter is permanently attached to the tip of said housing. Said catheter has a gauge size corresponding to the gauge of said needle. When said plunger is fully inserted into said housing, said introducing needle extends through said flexible catheter with the point of said needle extending beyond the venous end of said catheter. When said plunger is in the fixed retracted position, a continuous path for conducting the flow of fluids is provided extending from the venous end of the catheter through the catheter, through a portion of the tip, through said introducing needle, through the plunger and exiting the intravenous tubing line opening of said plunger.

BRIEF DESCRIPTION OF THE DRAWINGS

FIG. 2 and FIG. 3 are longitudinal cut-away views of the catheter device, showing the introducing needle before use and after use, respectively.

DETAILED DESCRIPTION OF THE INVENTION

Figure 1:
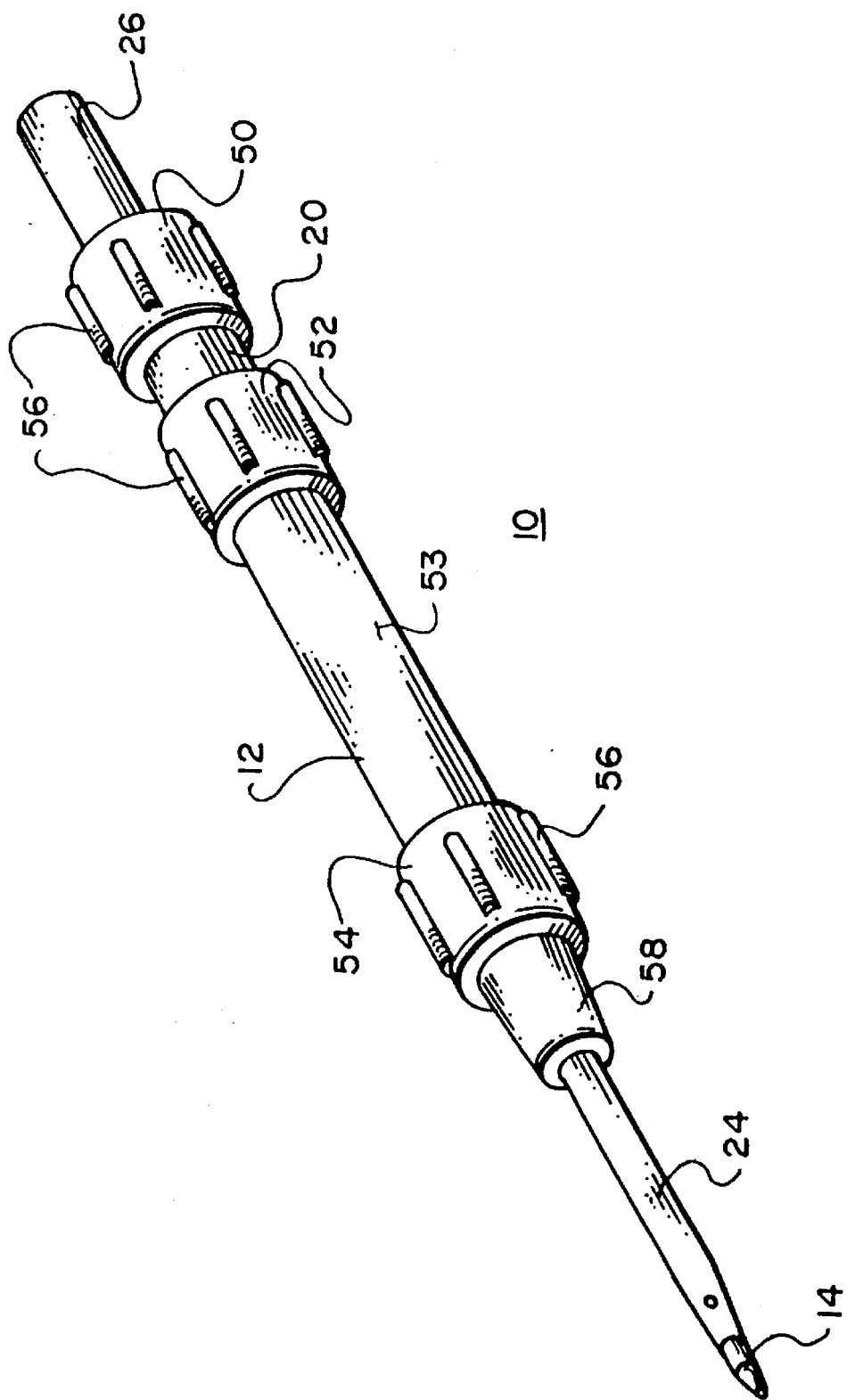
FIG. 1 is an isometric view of the catheter apparatus in accordance with the invention.

FIG. 1 is an isometric view of catheter apparatus 10. The material selected for the construction of the invention are preferably plastics of the type that is typically used for constructing such medical devices. The external shape of the invention, including housing 12, is preferably cylindrical but other cross-sectional shapes would be acceptable.

Housing 12 is externally made up of tip 58, insertion collar 54, barrel 53, and housing retraction collar 52. A plurality of grips 56 are longitudinally place along collars 54 and 52. The diameter of housing 12 and its associated component parts are not critical and can be sized similar to present catheter devices. In this manner, medical personnel will be instantly comfortable with the use of the invention without needing to be accustomed to a differently sized apparatus.

Housing 12 can be manufactured in a number of ways, however, the most practical from a cost and quality perspective is to inject mold the unit. With the exception of tip 58, which is preferably color coded to indicate gauge size, housing 12 should be substantially translucent to permit medical personnel to detect blood flashback.

Fitted within housing 12 at tip 58 is catheter 24. Catheter 24 is preferably flexible tubing of a type that is typical for use in catheters such as Teflon. Any materials that have been approved for catheter use are acceptable. Catheter 24 is attached within tip 58 using techniques well known in the art such as electro-welding.

Slidably mounted within housing 12 is plunger 20. Attached to plunger 20 is needle 14. Catheter 24 and needle 14 are sized so that needle 14 can be used as an introduction needle for catheter 24. Attached to plunger 20 is plunger collar 50 which like its housing counterparts features grips 56. Attachment end 26 is provided at the end of plunger 20. Attachment end 26 is shaped and dimensioned so that a standard IV set (not shown) can be attached.

FIG. 2 is a longitudinal cut-away side view of catheter apparatus 10, showing needle 14 before use. Within tip 58 is bore 61 which is sized so that needle 14 can slide through yet be sufficiently tight to keep needle 14 rigidly aligned within housing 12 and prevent fluid from leaking between needle 14 and tip 58. As noted above, needle 14 is firmly attached to plunger 20. Opening 62 is provided within plunger which serves to direct fluid flow from needle 14 to attachment end 26.

Locking fingers 22 are attached to the inside wall 63 of barrel 53. The number of locking fingers 22 is not critical but at least two is preferable so that plunger 20 will be symmetrically held within housing 12. Locking fingers 22 are resilient metal or plastic projections which can be easily flexed by plunger head 28 as plunger 20 is retracted from housing 12. Head 28 is preferably chamfered at corner 64 so that fingers 22 can easily move around head and be locked in position on surface 65 of head 28, once plunger 20 is fully retracted as shown in FIG. 3.

To use catheter apparatus 10, an IV set is attached to attachment end 26. An operator grasps housing 12 via insertion collar 54 and inserts needle 14 and the attached catheter 24 into a vein or fistula of the patient. The operator then retracts plunger 20 by grasping housing retraction collar 52 with one hand and plunger collar 50 with the other hand. Simultaneously, the retraction of plunger 20 retracts needle 14 through bore 61. Recall that bore 61 is dimensioned so that fluid cannot leak past needle 14. As plunger 20 and attached plunger head 28 are further retracted, locking fingers 22 are pried apart, sliding over chamfer 64, until plunger head 28 moves past fingers 22. At that point, locking fingers 22 snap back to their original positions locking head 28 in position via surface 65, thus preventing plunger head 28 being pushed in the reverse direction. Plunger stop 18 prevents plunger head 28 from being retracted completely out of housing 12. At this point, shown in cross-section in FIG. 3, needle 14 is completely enclosed and securely locked within housing 12 and bore 61. Catheter 24 can be advanced into vein or fistula by advancing collar 54. Also, since an IV tubing line is connected to attachment end 26, the medical procedure such as hemodialysis can be immediately initiated without having to break the line with the attendant risk of contamination. Once the procedure is completed, catheter apparatus 10 can be removed from the patient's vein and discarded, knowing that tip 66 of needle 14 is still completely enclosed and securely locked within housing 12 and bore 61.

Figure 5:
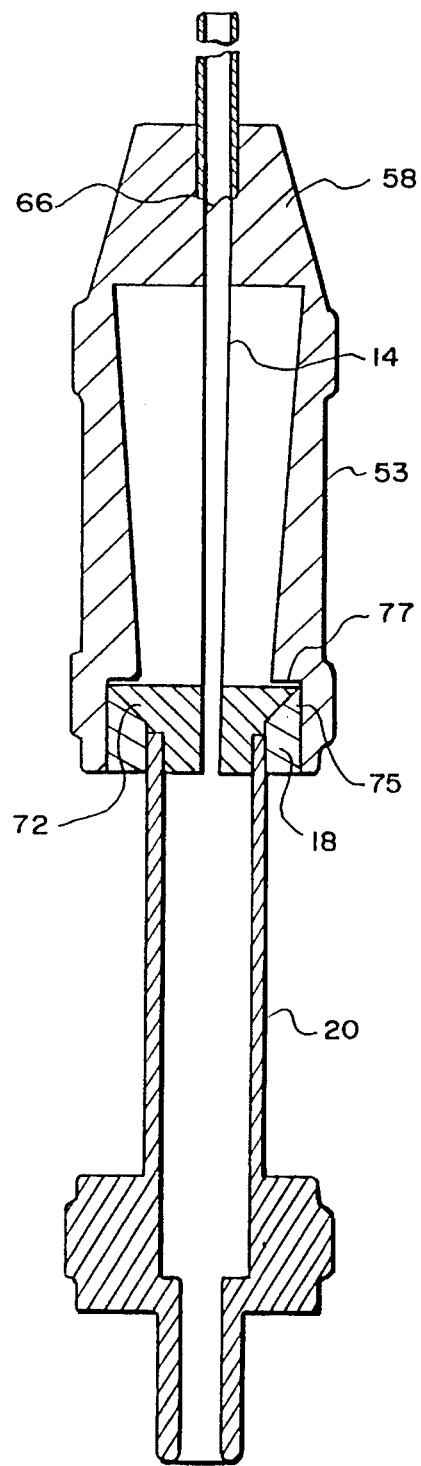
FIG. 4 and FIG. 5 are longitudinal cut-away views of an alternative embodiment of the invention.
Figure 4:
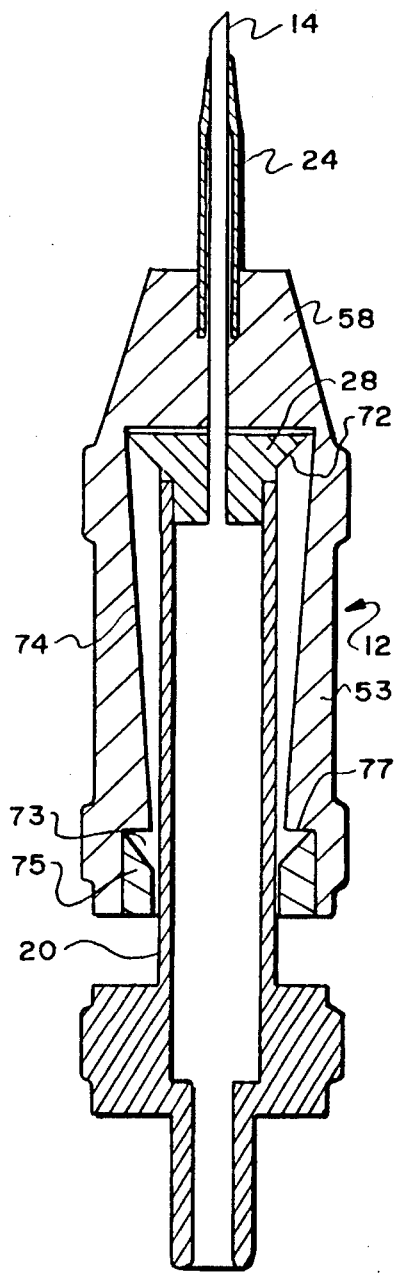

FIG. 4 is a longitudinal cut-away side view of an alternative embodiment of catheter apparatus 10, showing needle 14 before use. Housing 12 contains substantially hollow plunger 20, to which needle 14 is attached. In this embodiment, plunger head 28 is modified to flared end 72. Since head 28 is preferably a compliant material such as rubber, end 72 will be compressed as plunger 20 is withdrawn, urged by taper 74 of barrel 53. Once plunger 20 is in a fully retracted state as shown in FIG. 5, plunger 20 is locked by flared end 72 being held within notch 73, formed by incline 75 of stop 18 and surface 77 of barrel 53. As in the preferred embodiment, the operator is prevented from a needlestick since tip 66 of needle 14 is completely enclosed within tip 58.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. An apparatus for intravenous medical procedures comprising:

a cylindrical housing having a barrel with an interior cross-section and an interior tapered wall and having a tip at one end and a plunger opening at the other end, and with the tip of said housing having a tip bore with a diameter and with the tip bore extending into the barrel of said housing, said barrel being substantially translucent such that blood flashback is detectable;

a cylindrical plunger having a needle opening, an inserted position, a retracted position, and an intravenous tubing line opening, said plunger having an exterior cross-section corresponding to the interior cross-section of the barrel of said housing;

an introducing needle having a point and a gauge size corresponding to the diameter of the tip bore, said needle being rigidly connected to the needle opening of said plunger, such that when said plunger is fully inserted into the barrel of said housing, said needle extends through said tip bore;

locking means, connected between said plunger and said housing, for holding said plunger in a fixed retracted position relative to said housing such that when said plunger is in the fixed retracted position, the point of said introducing needle is held within the tip bore of said housing;

a compliant head attached adjacent to the needle opening of said plunger and a recess within the interior tapered wall of said barrel, with said recess adjacent to the plunger opening of said housing such that when said plunger is retracted, said head is compressed by the tapered wall of said barrel until said head engages said recess thus locking said plunger in a fixed position with the point of said needle within the tip bore;

at least one collar on said housing and at least one collar on said plunger, said collars having a plurality of grips that facilitate the insertion and retraction of said plunger into said barrel;

a flexible catheter, having a venous end and an attachment end, with the attachment end of said catheter permanently attached to the tip of said housing, said catheter having a gauge size corresponding to the gauge of said needle, such that when said plunger is fully inserted into said housing, said introducing needle extends through said flexible catheter with the point of said needle extending beyond the venous end of said catheter and such that when said plunger is in the fixed retracted position, a continuous path for conducting the flow of fluids is provided extending from the venous end of the catheter through the catheter, through a portion of the tip, through said introducing needle, through the plunger and exiting the intravenous tubing line opening of said plunger.

* * * * *